United States Patent [19]

Quirk

[11] Patent Number: 4,861,925
[45] Date of Patent: Aug. 29, 1989

[54] PROCESS FOR THE PREPARATION OF NITROOLEFINS

[75] Inventor: Jennifer M. Quirk, Highland, Md.

[73] Assignee: W. R. Grace & Co.-Conn., New York, N.Y.

[21] Appl. No.: 219,682

[22] Filed: Jul. 15, 1988

[51] Int. Cl.⁴ .................................... C07C 79/08
[52] U.S. Cl. ........................... 568/942; 568/943; 568/924
[58] Field of Search ............. 260/688; 568/942, 943, 568/944, 947, 924, 927, 946, 948, 945

[56] References Cited

U.S. PATENT DOCUMENTS

| | | | |
|---|---|---|---|
| 2,414,594 | 1/1947 | Gold | 568/943 |
| 3,240,823 | 3/1966 | Bonetti et al. | 568/927 |
| 3,255,263 | 6/1966 | Abbott | 568/943 |
| 3,510,531 | 5/1970 | Larkin et al. | 568/943 |
| 4,384,149 | 5/1983 | Suzuki | 568/943 |

FOREIGN PATENT DOCUMENTS

| | | |
|---|---|---|
| 125250 | 1/1959 | U.S.S.R. |
| 154253 | 3/1962 | U.S.S.R. |

OTHER PUBLICATIONS

*Nitration of Hydrocarbons* A. V. Topchiev, Pergamon Press, New York, 1959, pp. 193–199.
*Unsaturated Nitro Compounds*, V. V. Perekalin, Daniel Davey & Co., Inc., New York, 1964, pp. 15–31.

*Primary Examiner*—John F. Terapane
*Assistant Examiner*—Susan Wolffe
*Attorney, Agent, or Firm*—James P. Barr

[57] ABSTRACT

A process for the preparation of nitroolefins which comprises heating a solution of a nitroalcohol of the formula:

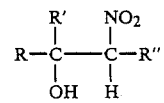

to at least 125° C. to give a corresponding nitroolefin which is contacted in situ with nucleophilic addition reagent.

20 Claims, No Drawings

PROCESS FOR THE PREPARATION OF NITROOLEFINS

BACKGROUND OF THE INVENTION

The present invention relates to a simple, one-step process for the preparation of nitroolefins by thermal dehydration of vicinal nitroalcohols.

Nitroolefins have been prepared by various methods known in the art. For example, U.S. Pat. No. 4,384,149 teaches a process for the preparation of one nitroalkene by the reaction of one alkene with dinitrogen tetraoxide in the presence of oxygen and an ether solvent to form an alkene-dinitrogen tetraoxide adduct and subsequent reaction of this adduct with sodium fluoride in the presence of an inert gas. Another method is to contact olefins with nitric oxide in the presence of an ether solvent as taught by U.S. Pat. No. 3,658,922.

Thermal dehydration of aryl nitroalcohols at high temperatures is known to produce nitroolefins in high yields. However, similar attempts to thermally dehydrate alkyl or alkyl-substituted nitro alcohols have not resulted in the production of the desired nitroolefin but, instead, provides various condensation products. To avoid these unfavorable reaction conditions, U.S. Pat. No. 2,414,594, and USSR Pat. Nos. 125,250 and 154,253 teach that the nitroolefin can be produced by the initial formation of a nitroacetate which can generate the nitroolefin through the elimination of acetic acid. An alternative method is to employ the use of catalysts. For example, U.S. Pat. Nos. 3,240,823 and 3,510,531, teach the use of alumina as a catalyst for the dehydration of nitroalcohols to the corresponding nitroolefin at temperatures between 50° and 150° C.

An object of this invention is to provide a new and improved process for the production of various types of nitroolefins. A further object is to provide a simple, one-step process for the production of nitroolefins without the requirement of catalysts.

The above objects are accomplished, as evidenced by the present invention without the need of catalysts nor a multistep process as, for example, initially forming nitroacetates from nitroalcohols with subsequent removal of acetic acid.

SUMMARY OF THE INVENTION

It has now been found that non-aryl nitroalcohols can be thermally dehydrated to form nitroolefins in high yields by a process which comprises:

heating a solution of a nitroalcohol to temperatures of at least 125° C. to form a corresponding nitroolefin in the presence of a facile nucleophilic addition reactant.

DETAILED DESCRIPTION

The subject process is directed to a means of readily providing non-aryl nitroolefins in high yields which can be further reacted into various desired products.

The nitroalcohols capable of being converted by the present process can be represented by the formula

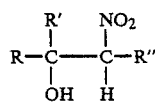

wherein R, R' and R" are each independently selected from hydrogen, alkyl, or cycloalkyl group. The preferred nitroalcohols have at least one of the groups R, R' and R" selected from an alkyl group, preferably a $C_1$–$C_{20}$ alkyl and most preferably a $C_1$–$C_3$ alkyl group.

A solution of nitroalcohol is subjected to elevated temperature of at least 125° C. and preferably from 150° C. to 200° C. The nitroalcohol substrate should be in a solution in which the substrate is present in concentrations of from 5 to 50 percent by weight based on the total weight of the solution.

The solution should further contain a nucleophilic reagent. The concentration of these nucleophilic reagents should be equal to or greater than the mole percentage of nitroalcohol.

Thus the undesirable nitroolefin polymerization products are effectively avoided by the utilization of nucleophilic reactants which trap the nitroolefin by addition reactions across the olefinic double bond. Typical nucleophilic addition reactions include, but are not limited to: additions of thiols such as methane thiol, ethane thiol, 2-propanethiol, 1-propanethiol, 2-methyl-2-propanethiol, 2-butanethiol, 2-methyl-1-propanethiol, 1-butanethiol, 1-pentanethiol, 2-pentanethiol, 3-pentanethiol, and hydrogen sulfide; ammonia; amines such as methylamine, ethylamine, diethylamine, propylamine, dipropylamine, methylethylamine; aniline and other nitrogenous bases; Diels Alder type conjugated dienes such as 1,3-butadiene or isoprene, 1,3-pentadiene, 2,4-hexadiene, 2-methyl-1,3-pentadiene, 2-methyl-2,4-hexadiene, 2-ethyl-1,3-pentadiene and 3-methyl-2,4-hexadiene and the like, and other suitable Michael reaction type reactants such as alkali or alkaline earth metal alkoxides, methoxide, ethoxide, propoxide, isopropoxide, 1-butoxide, 2-butoxide, 1-pentoxide and 2-pentoxide; nitroparaffins such as nitromethane, nitroethane, 1-nitropropane, 2-nitropropane, 2-nitrobutane, 2-nitropentane, 3-nitropentane, 2-nitro-3-methylpentane, 2-nitro-3-methylbutane and 2-methyl-3-nitropentane These reactions produce β-Alkylthio, β-amino and similar β-substituted nitroalkanes, nitro cyclohexenes, and dinitro alkanes. These may serve as intermediates in the synthesis of amino ethers, amino thioethers, diamines, etc.

The solvent can be any inert liquid capable of solubilizing the nitroalcohol and the nucleophilic reagent and capable of remaining liquid under reaction conditions. Examples of suitable inert liquid solvents are hexane, acetonitrile, toluene, or tetrahydrofuran, and preferably methanol or ethanol.

The solutions can be heated at ambient or elevated pressure in order to maintain liquid solution. Normally pressures of from 15 to 200 psi are used.

A first embodiment of the invention is directed to the process where the nitroalcohol is thermally dehydrated to form the corresponding nitroolefin of the formula:

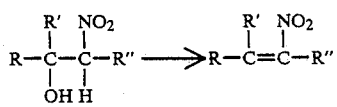

where R, R' and R" are H or non-aryl organic moieties, and are trapped in situ via a Diels Alder reaction:

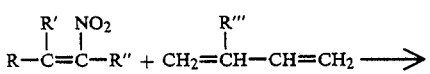

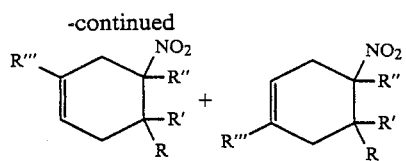

where R''' is a hydrogen, alkyl, cycloalkyl or aryl group.

Typical Diels - Alder reactants are 1,3-butadiene, isoprene, 1,3-pentadiene, 2,4-hexadiene, 2-methyl-1,3-pentadiene, 2-methyl-2,4,hexadiene, 2-ethyl-1,3-pentadiene and 2-ethyl-2,4-hexadiene, and the like.

A second embodiment of this invention is directed to the process where the nitroalcohol, is thermally dehydrated as in the first embodiment, and is trapped in situ via a Michael reaction of the formula:

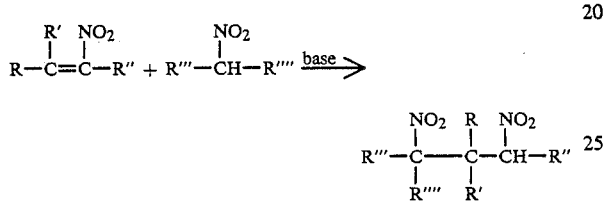

where R''' and R'''' are independently selected from hydrogen, alkyl, cycloalkyl or aryl group.

A third embodiment of this invention is directed to trapping the nitroolefin via a Michael reaction as in the second embodiment, but where the nucleophilic addition reagent is an amine. This reaction may be illustrated by the formula:

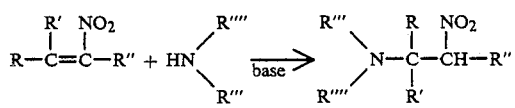

where R''' and R'''' are independently selected from hydrogen, alkyl, cycloalkyl or aryl groups.

A fourth embodiment of this invention is directed to trapping the nitroolefin via a Michael reaction as in the third embodiment but where the nucleophilic addition reagent is a thiol. This reaction may be illustrated by the formula:

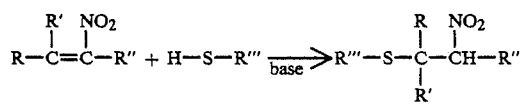

where R''' is a hydrogen, alkyl, cycloalkyl or aryl group.

A fifth embodiment of this invention is directed to trapping the nitrolefin via a Michael reaction as in the third embodiment but where the nucleophilic addition reagent is an alkoxide. The reaction may be illustrated by the formula:

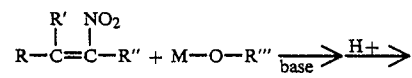

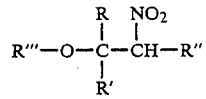

where R''' is an alkyl, cycloalkyl, or aryl group and M is an alkali or alkaline earth metal.

The following examples are provided to illustrate the invention in accordance with the principles of this invention but are not to be construed as limiting the invention in any way except as indicated in the appended claims. All parts and percentages are by weight unless otherwise indicated.

EXAMPLE I

To a 50 ml Hoke cylinder was added 2 g (0.017 mol) 2-nitrobutanol, 2.5 g (0.037 mol) isoprene and 5 ml methanol as a solvent. The reaction was heated to 150° C. for 14 hours. The reaction mixture, analyzed by gas chromatography, showed that a mixture of 2-methyl-4-ethylnitrocyclohexene and 1-methyl-4-ethyl-4-nitrocyclohexene had been formed in a yield of 87%.

EXAMPLE II

To a 50 ml Hoke cylinder was added 2.0 g (0.017 mol) 2-nitro-3-butanol, 2.5 g (0.037 mol) isoprene and 5 ml methanol as a solvent. The reaction was heated to 150° C. for 8 hours. Gas chromatography showed that a mixture of 2,4,5-trimethyl-4-nitrocyclohexene and 1,4,5-trimethylcyclohexene had been found in a 53% yield.

EXAMPLE III

To a 50 ml Hoke cylinder was added 2.0 g (0.019 mol) 2-nitropropanol, 2.5 g (0.037 mol) isoprene and 5.0 ml methanol as a solvent. The reaction was heated to 150° C. for 12 hours. Gas chromatography and mass spectroscopy confirmed that a mixture of 2,4-dimethyl-4-nitrocyclohexene and 1,4-dimethyl-4-nitrocyclohexene had been formed in a 72% yield.

EXAMPLE IV

To a 50 ml Hoke cylinder was added 0.5 g (0.0047 mol) 2-nitropropanol, 1.0 g (0.011 mol) 2-nitropropane, 0.1 g triethylamine and 7 ml methanol as a solvent. The reaction was heated to 125° C. for 8 hours. Gas chromatography and mass spectroscopy confirmed that 2,4-dinitro-2-methylpentane had been formed in a 67% yield.

EXAMPLE V

The reaction was run as in Example 1 using nitroethanol, isoprene and methanl as a solvent. Gas chromatography and mass spectroscopy confirmed that a mixture of 2-methyl-4-nitrocyclohexene and 1 methyl-4-nitrocyclohexene had been formed in a 72% yield.

EXAMPLE VI

The reaction was run as in Example 1, using 2-nitrobutanol, 1,3-butadiene and methanol as a solvent. Gas chromatography and mass spectroscopy confirmed that 4-nitrocyclohexene had been formed in an 81% yield.

What is claimed is:

1. A process for the preparation of nitroolefins consisting essentially of:

(a) mixing a nucleophilic addition reagent and a itroalcohol, said nitroalcohol having the formula

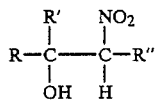

wherein R, R' and R" are independently selected from hydrogen, alkyl or cycloalkyl, heating the mixture to a temperature of at least 125° C. to dehydrate the nitroalcohol to form a corresponding nitroolefin, the nucleophilic addition reagent trapping the nitroolefin in situ to form an addition product; and (b) separating said addition product.

2. A process for the preparation of nitroolefins as recited in claim 1, wherein R, R' and R" are hydrogen.

3. A process for the preparat,ion of nitroolefins as recited in claim 1, wherein R and R' are hydrogen and R" is selected from a $C_1$–$C_{20}$ alkyl.

4. A process for the preparation of nitroolefins as recited in claim 1, wherein R and R' are hydrogen and R" is selected from methyl or ethyl.

5. A process for the preparation of nitroolefins as recited in claim 1, wherein R' is hydrogen and R and R" are each selected from a $C_1$–$C_{20}$ alkyl.

6. A process for the preparation of nitroolefins as recited in claim 1, wherein R' is hydrogen and R and R" are each selected from methyl or ethyl.

7. A process for the preparation of nitroolefins as recited in claim 1, wherein each R, R' and R" is independently selected from a $C_1$–$C_{20}$ alkyl.

8. A process for the preparation of nitroolefins as recited in claim 1, wherein each R, R' and R" is independently selected from methyl or ethyl.

9. A process for the preparation of nitroolefins as recited in claim 1, wherein the nucleophilic reagent is selected from the group consisting of dienes, nitroparaffins, amines, thiols, and alkoxides.

10. A process as recited in claim 9 wherein the diene is selected from the group consisting of 1,3-butadiene, isoprene, 1,3-pentadiene, 2,4-hexadiene, 2-methyl-1,3-pentadiene, 2-methyl-2,4-hexadiene, 2-ethyl-1,3-pentadiene and 3-methyl-2,4-hexadiene.

11. A process as recited in claim 9 wherein the nitroparaffin is selected from the group consisting of nitromethane, nitroethane, 1-nitropropane, 2-nitropropane, 2-nitrobutane, 2-nitropentane, 3-nitropentane, 2-nitro-3-methylpentane, 2-nitro-3-methylbutane and 2-methyl-3-nitropentane.

12. A process as recited in claim 9 wherein the amine is selected from the group consisting of methylamine, dimethylamine, ethylamine, diethylamine, propylamine, dipropylamine, methylethylamine, ammonia, and aniline.

13. A process as recited in claim 9 wherein the thiol is selected from the group consisting of methane thiol, ethane thiol, 2-propanethiol, 1-propanethiol, 2-methyl-1-propanethiol, 2-butanethiol, 2-methyl-1-propanethiol, 1-butanethiol, 1-pentanethiol, 2-pentanethiol, 3-pentanethiol, and hydrogen sulfide.

14. A process as recited in claim 9 wherein the alkoxide is selected from the group consisting of methoxide, ethoxide, propoxide, isopropoxide, 1-butoxide, 2-butoxide, 1-pentoxide and 2-pentoxide.

15. A process for the preparation of nitroolefins as recited in claim 1 wherein the nitroalcohol is 2-nitrobutanol and the nucleophilic addition reagent is isoprene.

16. A process for the preparation of nitroolefins as recited in claim 1 wherein the nitroalcohol is 2-nitro-3-butanol and the nucleophilic addition reagent is isoprene.

17. A process for the preparation of nitroolefins as recited in claim I wherein the nitroalcohol is 2-nitropropanol and the nucleophilic addition reagent is isoprene.

18. A process for the preparation of nitroolefins as recited in claim 1 wherein the nitroalcohol is 2-nitropropanol and the nucleophilic addition reagent is 2-nitropropane.

19. A process for the preparation of nitroolefins as recited in claim 1 wherein the nitroalcohol is nitroethnaol and the nucleophilic addition reagent is isoprene.

20. A process for the preparation of nitroolefins as recited in claim 1 wherein the nitroalcohol is 2-nitrobutanol and the nucleophilic addition reagent is 1,3-butadiene.

* * * * *

UNITED STATES PATENT AND TRADEMARK OFFICE
CERTIFICATE OF CORRECTION

PATENT NO. : 4,861,925
DATED : August 29, 1989
INVENTOR(S) : J. M. Quirk

It is certified that error appears in the above-identified patent and that said Letters Patent is hereby corrected as shown below:

Col. 5, line 2 delete "itroalcohol" insert therefor --nitroalcohol--.

Col. 5, line 21 delete "preparat,ion" insert therefor --preparation--.

Col. 6, line 17 delete "1-propanethiol" insert therefor --2-propanethiol--.

Col. 6, line 33 after the word "claim" delete "I" and insert therefor --1--.

Signed and Sealed this

Nineteenth Day of June, 1990

Attest:

HARRY F. MANBECK, JR.

*Attesting Officer*     *Commissioner of Patents and Trademarks*